United States Patent
Torgerson et al.

(10) Patent No.: US 8,925,493 B2
(45) Date of Patent: Jan. 6, 2015

(54) HOOF BATH SYSTEM

(75) Inventors: Kevin L. Torgerson, Holmen, WI (US);
Robert L. Buck, Holmen, WI (US);
Nathan Hedlund, Lewiston, MN (US);
Sue Mendell, Onalaska, WI (US);
Randal D. Stevenson, Cottage Grove,
WI (US); Charles D. Gradle, Oak Park,
IL (US); Alejandro O. Dee, Roselle, IL
(US); Jeffrey S. Hanson, Melrose, WI
(US); Glenn Gingrich, Trempealeau, WI
(US)

(73) Assignee: GEA Farm Technologies, Inc.,
Naperville, IL (US)

( * ) Notice: Subject to any disclaimer, the term of this patent is extended or adjusted under 35 U.S.C. 154(b) by 0 days.

(21) Appl. No.: 12/658,758

(22) Filed: Feb. 12, 2010

(65) Prior Publication Data
US 2010/0218731 A1   Sep. 2, 2010

Related U.S. Application Data

(63) Continuation of application No. 11/300,616, filed on Dec. 14, 2005, now Pat. No. 7,661,393.

(60) Provisional application No. 60/723,462, filed on Oct. 4, 2005.

(51) Int. Cl.
| | | |
|---|---|---|
| A01K 29/00 | (2006.01) | |
| A61K 31/366 | (2006.01) | |
| A61K 33/30 | (2006.01) | |
| A61D 11/00 | (2006.01) | |
| A01L 15/00 | (2006.01) | |
| A61K 33/24 | (2006.01) | |
| A61K 33/26 | (2006.01) | |
| A61K 45/06 | (2006.01) | |
| A61K 33/34 | (2006.01) | |
| A01K 13/00 | (2006.01) | |

(52) U.S. Cl.
CPC .............. *A61D 11/00* (2013.01); *A61K 31/366* (2013.01); *A61K 33/30* (2013.01); *A01L 15/00* (2013.01); *A61K 33/24* (2013.01); *A61K 33/26* (2013.01); *A61K 45/06* (2013.01); *A61K 33/34* (2013.01); *A01K 13/003* (2013.01)
USPC ........................................................ 119/673

(58) Field of Classification Search
USPC ......... 119/667, 669, 665, 671, 673, 678, 650, 119/651; 604/293; 4/574.1, 622; 137/172, 137/884, 861; 138/93; 251/61.1
See application file for complete search history.

(56) References Cited

U.S. PATENT DOCUMENTS

| | | |
|---|---|---|
| 870,766 A | 11/1907 | Eaton |
| 876,631 A | 1/1908 | Goff |

(Continued)

FOREIGN PATENT DOCUMENTS

| | | |
|---|---|---|
| CA | 2 471 434 A1 | 12/2002 |
| DE | 298 08 877 U1 | 8/1998 |

(Continued)

OTHER PUBLICATIONS

DeLaval Foot Bath AFB1000™, brochure, 2pp.

(Continued)

*Primary Examiner* — Trinh Nguyen
(74) *Attorney, Agent, or Firm* — Smith Law Office

(57) ABSTRACT

The present invention is directed to methods for applying bovine foot and hoof treatment compositions having two or more specific and complimentary antimicrobial components in a hoof bath just prior to use to work more effectively. These antimicrobial components may include antimicrobial inorganic salts of certain heavy metals, cationic agents, peroxides, aldehydes, fatty acids, iodines or other suitable compounds effective in the killing of microorganisms.

12 Claims, 17 Drawing Sheets

(56) References Cited

U.S. PATENT DOCUMENTS

| | | | |
|---|---|---|---|
| 876,632 | A | 1/1908 | Goff |
| 883,132 | A | 3/1908 | Goff |
| 1,511,450 | A | 10/1924 | Findlay |
| 2,264,201 | A | 11/1941 | Findlay |
| 2,439,866 | A | 4/1948 | Saladin |
| 2,499,174 | A | 2/1950 | Turner |
| 2,542,280 | A | 2/1951 | Knapp |
| 2,870,478 | A | 1/1959 | Schuster |
| 3,027,568 | A | 4/1962 | Blau et al. |
| 3,060,892 | A | 10/1962 | Schantz |
| 3,062,188 | A | 11/1962 | O'Day |
| 3,173,402 | A | 3/1965 | Cassel |
| 3,272,201 | A | 9/1966 | Burns |
| 3,380,080 | A | 4/1968 | Farrell |
| 3,496,914 | A | 2/1970 | Cowan |
| 3,734,057 | A | 5/1973 | Lee et al. |
| 3,741,201 | A | 6/1973 | Oudkerk |
| 3,863,275 | A * | 2/1975 | Brendgord et al. ............... 4/556 |
| 4,020,796 | A | 5/1977 | Grifa |
| 4,039,452 | A | 8/1977 | Fernandez |
| 4,047,522 | A | 9/1977 | Plugge |
| 4,090,507 | A | 5/1978 | Van Horn |
| 4,122,869 | A * | 10/1978 | Roberson, Sr. ................. 138/93 |
| 4,126,104 | A | 11/1978 | Overby |
| 4,165,714 | A | 8/1979 | Weissman et al. |
| 4,183,329 | A | 1/1980 | Leonaggeo, Jr. |
| 4,197,597 | A | 4/1980 | Toms |
| 4,317,431 | A | 3/1982 | Sparkes |
| 4,379,440 | A | 4/1983 | Thedford et al. |
| 4,485,503 | A | 12/1984 | Rolando et al. |
| 4,497,313 | A | 2/1985 | Kurosawa |
| 4,510,889 | A | 4/1985 | Jobe |
| 4,513,735 | A | 4/1985 | Friedson et al. |
| 4,577,624 | A | 3/1986 | Patton |
| 4,660,506 | A | 4/1987 | Nalven |
| 4,876,753 | A | 10/1989 | Bucher |
| 4,907,305 | A | 3/1990 | Teramachi et al. |
| 4,917,125 | A | 4/1990 | Midkiff |
| 4,942,868 | A | 7/1990 | Vago |
| 5,010,605 | A | 4/1991 | Shiina et al. |
| 5,048,463 | A | 9/1991 | Wilson et al. |
| 5,048,520 | A | 9/1991 | Vago |
| 5,063,880 | A | 11/1991 | Bouthillier |
| 5,098,415 | A | 3/1992 | Levin |
| 5,178,134 | A | 1/1993 | Vago |
| 5,290,437 | A | 3/1994 | Lin |
| 5,305,737 | A | 4/1994 | Vago |
| 5,341,828 | A | 8/1994 | Ferguson, Sr. |
| 5,367,720 | A | 11/1994 | Stephens et al. |
| 5,419,347 | A | 5/1995 | Carruth |
| 5,608,927 | A | 3/1997 | Lowry et al. |
| 5,630,379 | A * | 5/1997 | Gerk et al. .................... 119/667 |
| 5,758,603 | A | 6/1998 | Vivier |
| 5,774,909 | A | 7/1998 | Stable |
| 5,784,998 | A | 7/1998 | Manzer |
| 5,842,442 | A | 12/1998 | Marr |
| 6,029,610 | A | 2/2000 | Ramsey et al. |
| 6,382,136 | B1 * | 5/2002 | Bragulla et al. ............... 119/650 |
| 6,497,822 | B2 | 12/2002 | Blanchette et al. |
| 6,520,118 | B2 | 2/2003 | Swiegers et al. |
| 6,699,510 | B2 | 3/2004 | McSherry et al. |
| 6,739,286 | B2 | 5/2004 | Vander Veen |
| 6,818,212 | B2 | 11/2004 | Johansen |
| 6,827,849 | B2 | 12/2004 | Kurokawa et al. |
| 6,875,364 | B2 | 4/2005 | Gordon |
| 7,661,393 | B2 | 2/2010 | Torgerson et al. |
| 7,798,104 | B2 | 9/2010 | Rajkondawar et al. |
| 2004/0053799 | A1 | 3/2004 | Collin |
| 2004/0216692 | A1 | 11/2004 | Vander Veen |
| 2005/0268977 | A1* | 12/2005 | Beaty ........................... 137/883 |
| 2007/0017576 | A1* | 1/2007 | McHinnis et al. ....... 137/247.51 |
| 2008/0196674 | A1 | 8/2008 | Buck et al. |
| 2009/0283053 | A1 | 11/2009 | Torgerson et al. |
| 2011/0000439 | A1 | 1/2011 | Rajkondawar et al. |

FOREIGN PATENT DOCUMENTS

| | | |
|---|---|---|
| DE | 29808877 | 8/1998 |
| DE | 100 58 363 A1 | 6/2002 |
| DE | 10058363 | 6/2002 |
| EP | 0 645 131 B1 | 3/1997 |
| EP | 0645131 | 3/1997 |
| EP | 1 099 373 A1 | 5/2001 |
| EP | 1099373 | 5/2001 |
| EP | 1 238 581 A2 | 9/2002 |
| EP | 1238581 | 9/2002 |
| EP | 1 384 400 A2 | 1/2004 |
| EP | 1384400 | 1/2004 |
| FR | 937 716 | 8/1948 |
| FR | 937716 | 8/1948 |
| GB | 1 595 893 | 9/1981 |
| GB | 1595893 | 9/1981 |
| GB | 2 275 860 A | 9/1994 |
| GB | 2 311 202 A | 9/1994 |
| GB | 2275860 | 9/1994 |
| GB | 2311202 | 9/1997 |
| GB | 2 398 220 A | 8/2004 |
| GB | 2398220 | 8/2004 |
| NL | 1009895 C | 2/2000 |
| NL | 1017154 C | 7/2002 |
| SU | 597899 | 3/1978 |
| WO | WO93/01763 | 2/1993 |
| WO | WO 93/01763 | 2/1993 |
| WO | WO93/08764 | 5/1993 |
| WO | WO 93/08764 | 5/1993 |
| WO | WO 00/28917 | 5/2000 |
| WO | WO00/28917 | 5/2000 |
| WO | WO03/056918 | 7/2003 |
| WO | WO 03/056918 A2 | 7/2003 |
| WO | WO2007/044372 | 4/2007 |
| WO | WO2007/070655 | 6/2007 |

OTHER PUBLICATIONS

PediCuRx Footbath Equipment, www.westfalia.com, 4pp.
English translation of SU 597899, 1p.
English language Abstract of AU 2002367388 A1, European Patent Office's esp@cenet.com database, 2pp.
English language Abstract, Translated Description and Claims of DE 100 58 363 A1, European Patent Office's esp@cenet.com database, 8pp.
English language Abstract of DE 29808877 U, European Patent Office's esp@cenet.com database 1 p.
English language Abstract of EP 1 465 479, European Patent Office's esp@cenet.com database, 1p.
English language Abstract, Translated Description and Claims of FR 937716, European Patent Office's esp@cenet.com database, 3pp.
English language Abstract of NL 1009895C, European Patent Office's esp@cenet.com database, 1p.
English language Abstract of NL 1017558C, European Patent Office's esp@cenet.com database, 1p.
Form PCT/ISA/220, Notification of Transmittal of the Int'l Search Report and the Written of Opinion of the Int'l Searching Authority, or the Decl. received May 14, 2007, 2pp.
Form PCT/ISA/210, International Search Report received May 14, 2007, 5pp.
Form PCT/ISA/237, Written Opinion received May 14, 2007, 7pp.
Form PCT/ISA/220, Notification of Trans. of the Int'l Search Report and the Written of Opinion of the Int'l Searching Authority, or the Decl. received Oct. 25, 2007, 2pp.
Form PCT/ISA/210, International Search Report received Oct. 25, 2007, 5pp.
Form PCT/ISA/237, Written Opinion received Oct. 25, 2007, 7pp.
PCT/IB/326, Notification Concerning Transmittal of International Preliminary Report on Patentability received Apr. 28, 2008, 1p.
PCT/IB/373, International Preliminary Report on Patentability received Apr. 28, 2008, 1p.
PCT/ISA/237, Written Opinion of the International Search Authority received Apr. 28, 2008, 7pp.
PCT/IB/326, Notification Concerning Transmittal of International Preliminary Report on Patentability received Jul. 3, 2008, 1p.

(56) References Cited

OTHER PUBLICATIONS

PCT/IB/373, International Preliminary Report on Patentability received Jul. 3, 2008, 1p.
PCT/ISA/237, Written Opinion of the International Searching Authority received Jul. 3, 2008, 6pp.
PCT/ISA/220, Notification of Transmittal of the International Search Report and the Written Opinion of the Int'l Searching Authority, or the Decl. received Mar. 23, 2009, 1p.
PCT/ISA/210, International Search Report received Mar. 23, 2009, 2pp.
PCT/ISA/237, Written Opinion of the International Searching Authority received Mar. 23, 2009, 6pp.
Notification Concerning Transmittal of International Preliminary Report on Patentability received Aug. 19, 2010, 1p.
PCT/IB/373, International Preliminary Report on Patentability received Aug. 19, 2010, 1p.
PCT/ISA/237, Written Opinion received Aug. 19, 2010, 4pp.
Office Action Summary for U.S. Appl. No. 11/300,616 dated Dec. 30, 2008, 5pp.
Office Action Summary for U.S. Appl. No. 12/012,798 dated Sep. 27, 2010, 24pp.
DeLaval Foot Bath AFB1000™, brochure, 2pgs. No Date Available.
English language Abstract of AU 002367388 A 1, European Patent Office's esp@cenet.com database, 2pgs.
English language Abstract of CA 2471 433, European Patent Office's esp@cenet.com database, 1 pg.
English language Abstract of DE 100 58 363 A 1, European Patent Office's esp@ceneLcom database, 1 pg.
English language Abstract of EP 1 465 479, European Patent Office's esp@cenet.com database, 1 pg.
English language Abstract of NL 1009895C, European Patent Office's esp@cenet.com database, 1 pg.
English lanugage Abstract of NL 1017558C, European Patent Office's esp@cenet.com database, 1 pg.
PCT/US06/38729, Int'l Search Report and Written Opinion received May 14, 2007 (Forms PCT/ISA/220, 210, and 237) 14 pgs.
Song, Jizhong "Trace elements and Foot/Hoof Diseases of Domestic Animals" Chinese Journal of Veterinary Sciences and Technology, Published Dec. 31, 1989, pp. 21-23, vol. 4, China.
Yu, Chunming "How to Prevent Limp by the Use of Hoof Bath" Shanghai Journal of Animal Husbandry and Veterinary Medicine, Published Dec. 31, 1987, vol. 2, Shanghai, China.

* cited by examiner

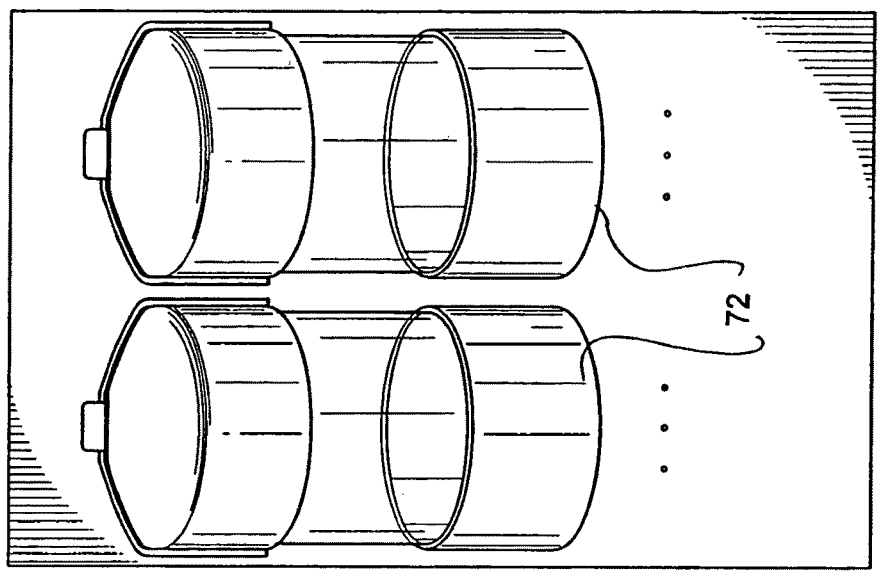
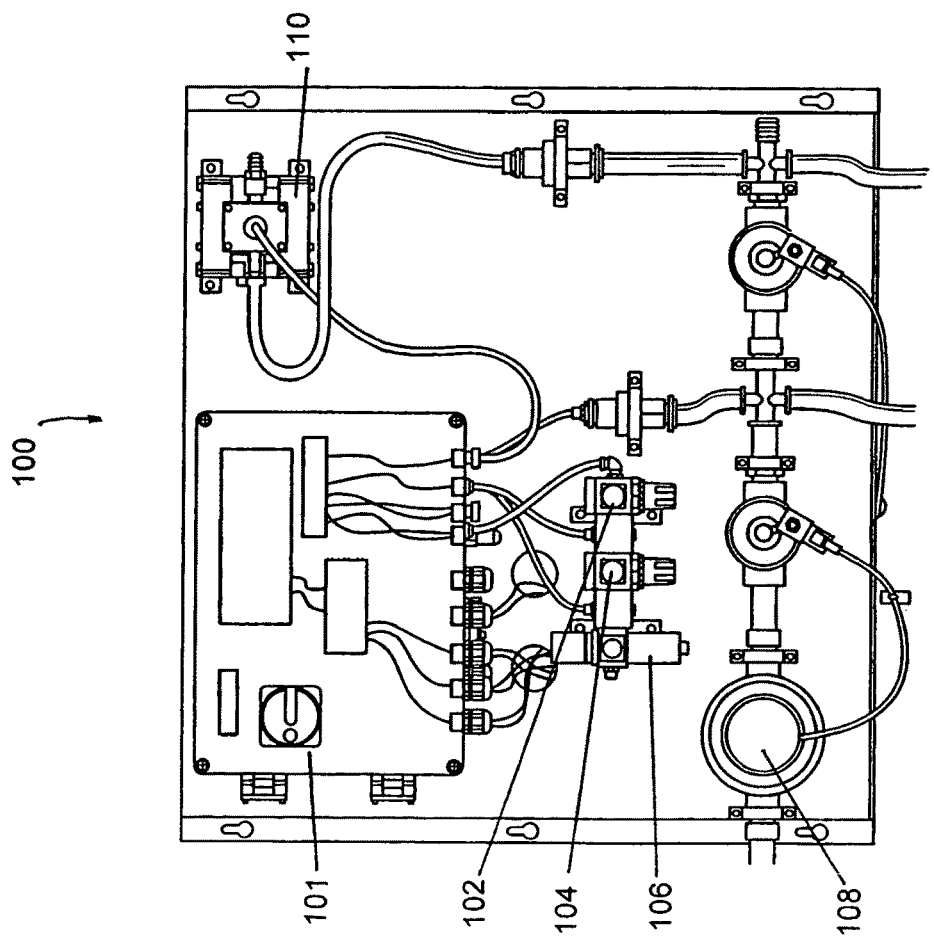
Fig. 15

PROGRAMMING

| NAME | DESCRIPTION | DEFAULT | UNITS |
|---|---|---|---|
| PT1 | BATH 2 CONFIGURATION | 0.0 | N/A |
| CC1 | NUMBERS OF CHEMICAL CANISTERS IN USE | 0.0 | N/A |
| T1 | DRAIN TIME BEFORE FLUSH | 25.0 | SECONDS |
| V2 | FLUSH WATER VOLUME | 5.0 | GALLONS |
| T2 | AIR PURGE TIME BATH 1 | 15.0 | SECONDS |
| T5 | AIR PURGE TIME BATH 2 | 15.0 | SECONDS |
| T4 | LIQUID CHEMICAL RUN TIME BATH 1 | 0.0 | SECONDS |
| T6 | LIQUID CHEMICAL RUN TIME BATH 2 | 0.0 | SECONDS |
| V1 | HALF OF BATH WATER FILL VOLUME | 18.0 | GALLONS |
| BT1 | TIME BETWEEN CHANGES OF BATH 1 | 7200.0 | SECONDS |
| BT2 | TIME BETWEEN CHANGES OF BATH 2 | 7200.0 | SECONDS |
| BC1 | NUMBER OF COWS BETWEEN CHANGES BATH 1 | 250.0 | SECONDS |
| BC2 | NUMBER OF COWS BETWEEN CHANGES BATH 2 | 250.0 | SECONDS |

Fig. 16

PLC CYCLE CHART

| OUTPUT | BATH 1 | | | | | | | | | | | | | | | |
|---|---|---|---|---|---|---|---|---|---|---|---|---|---|---|---|---|
| | DRAIN | FLUSH | | | FILL | | | | | | DRAIN | FLUSH | | | FILL | |
| | T1 | V2 | T2 | T3 | V1 / V3 | T4 | V1 | T2 | T7 | T1 | V2 | T5 | T3 | V1 / V3 | T6 | V1 | T5 | T7 |
| WATER FILL VALVE | | ▨ | | | | | ▨ | | | | ▨ | | | | | ▨ | | |
| AIR PURGE | | | | ▨ | | | | | ▨ | | | | ▨ | | | | | ▨ |
| BLADDER 1 | | | ▨ | | | | | | | | | ▨ | | | | | | |
| CHEMICAL 1 | | | | | | ▨ | | | | | | | | | | | | |
| BLADDER 2 | | | | | | | | | | | | ▨ | | | | | | |
| DECISION VALVE | | | | ▨ | ▨ | | | ▨ | ▨ | | | | ▨ | ▨ | ▨ | | | ▨ |
| CHEMICAL 2 | | | | | | | | | | | | | | | ▨ | | | |

POWDER DISPENSER OPTION ONLY

| BYPASS VALVE | | ▨ | | | ▨ | | ▨ | | | | ▨ | | | ▨ | | ▨ | | |
| FILL 1 | | | | | ▨ | ▨ | ▨ | ▨ | ▨ | | | | | ▨ | ▨ | ▨ | ▨ | ▨ |
| FILL 2 | | | | | | | | ▨ | ▨ | | | | | | ▨ | | ▨ | ▨ |
| FILL 3 | | | | | | | | | ▨ | | | | | | | | | ▨ |
| FILL 4 | | | | | | | | | | | | | | | | | | |

* THE BYPASS VALVE IS ONLY ENERGIZED IF THE WATER ONLY SWITCH IS ON. WHEN THE BYPASS VALVE IS ENERGIZED THE FILL VALVES WILL NOT BE ENERGIZED.

Fig. 17

HOOF BATH SYSTEM

This application is a continuation of application Ser. No. 11/300,616 filed Dec. 14, 2005 and claims the benefit of Provisional Application No. 60/723,462 filed Oct. 4, 2005, now U.S. Pat. No. 7,661,393 the disclosure of which are incorporated by reference herein.

FIELD AND BACKGROUND OF THE INVENTION

The present invention relates generally to hoof bath systems for dairy animals, and more particularly to a hoof bath system having in situ chemical mixing, chemical distribution for multiple hoof baths, and improved hoof bath components with improved hoof bath efficiency, efficacy, and automation.

The present invention also relates generally to bovine hoof treatments, and more specifically to bovine hoof treatment compositions and methods having two or more separate components mixed at the dairy to improve efficacy and safety to humans and animals.

Lameness is one of the major problems facing the dairy industry in the world today. The cost of lameness is measured by lost milk production, culled cows, dead cows, additional labor, vet bills, and medicines for treatment. In the U.S. alone, the cost of lameness has been reported to be between $300 and $412 per cow. With an overall estimated incidence rate of 10% to 15%, the annual overall cost of lameness would exceed 570 million dollars. It is especially a problem in large herds, which are the fastest growing segment of the market. The prevalence of lameness in large herds is 50% or more and is reflected by an annual incidence of 60% to 70%. Infectious diseases of the foot or hoof are one of the primary causes of lameness.

Studies have showed that fully a third of all lameness in cows is caused by one disease, digital dermatitis. Digital dermatitis is present worldwide and is estimated to be present in 41% of herds smaller than 100 cows and from 64% to 82% in larger herds. Contagious and debilitating diseases of the bovine foot and hoof include such conditions as bovine hoof rot, digital dermatitis and interdigital dermatitis.

Hoof baths containing germicidal/leaning chemicals and antibiotics and/or other biologics have been used on dairy operations in the attempt to prevent, control and treat these diseases. Hoof baths are generally located in the return alley of dairy milking barns or parlors. After being milked, the animal will typically walk through the hoof bath on the way back to where they are housed. The feet and hooves will many times contain accumulated dirt and manure, even after milking when at times the feet and hooves are sprayed with water or diluted chemicals. This is especially true in modern dairy facilities with housing contained in limited areas such as free stall or tie stall barns or dry lots instead of open pasture.

In addition, on passing through the hoof bath, the cows may defecate into the hoof bath. The added organic material or load to the hoof bath compromises the antimicrobial products' ability to work in the disinfection and cleansing of the cow feet where the causative microorganisms are located. For economic reasons, the use of antibacterial chemical and biological products in doses high enough to compensate for the organic material present in the hoof bath and to penetrate through organic material and whatever tissue may conceal or otherwise harbor the bacterial pathogens, is usually cost prohibitive. Other chemical products that are less expensive to use at higher doses have the disadvantage in that they may be toxic to the animals, the people working in the dairy facilities or the environment.

Also, many times when one product is used successfully (as in the treatment of digital dermatitis lesions) and the dose or frequency of the dose lessened after successfully eliminating the lesions, the clinical manifestations of the disease will reappear after a short time. One option utilized by many dairy producers is to alternate or rotate more than one chemical or antibiotic product at different times in the same hoof bath. There is at least anecdotal evidence that alternating different chemicals is effective in helping to reduce the incidence and prevalence of infectious diseases of the foot. However, this practice still does not compensate for the above-mentioned problems of using a high enough dose to overcome organic load while still producing a hoof bath that is safe and of low toxicity.

Prior hoof baths were typically recessed into the exit alley and were filled by hand or remotely through a system of pumps, pipes and valves. Dairy operators monitored the baths to determine when fresh chemicals and water needed to be added to the bath. Fresh bath water and chemicals are needed as chemicals lose their efficacy and/or the bath becomes fouled with dirt, debris, and manure.

To clear or flush dirt, debris, and manure from the baths, high pressure and high velocity water was pumped into the bath. Early hoof baths had an upstream end into which flushing water was pumped and a downstream end through which the flushing liquid and flushed materials flowed.

The downstream ends in some hoof bath systems were simple curbs or walls over which the fluid and material is forced by water pressure and/or velocity. Such systems tend to waste water and require unnecessarily high pump pressure. In addition, the inherent nature of a fixed curb can prevent all of the debris from being flushed from the bath.

Drains in the downstream end were added to some such systems to improve flushing performance. Some drains were manually operated, while others were automated to synchronize with flushing and re-filling operations.

In an attempt to further improve flushing performance, at least one system attempted to create specific current flows in the bath during flushing operations by using nozzles of varying jet velocities, sizes, and arrangements. See Vander Veen, U.S. Pat. No. 6,739,286. Such precision is difficult to maintain in actual dairy environments that are subject to harsh conditions, extreme temperature changes, and damage from animals.

As stated above, some hoof bath systems mix chemical and water in the bath. See Vander Veen, U.S. Pat. No. 6,739,286, for example. Such systems can be effective when a single hoof bath is used in a dairy, but using separate chemical and water dispensers in more than one hoof bath unnecessarily complicates piping, pumps, and valves. Duplicate dispensing systems also add expense in building and monitoring such systems. Malfunctions in such duplicative and complicated systems are inevitable.

Accordingly, there is a need for another way to bring safe, efficacious and cost effective doses of these products to the site of the microbial pathogens on the animal without being unduly hindered by organic material that may be present in the bath or on the foot. In addition, there is a need for a system-wide approach for operating hoof baths that reduces initial capital and maintenance expense.

SUMMARY OF THE INVENTION

A hoof bath system for dairy animals, the system comprising: an in situ chemical mixer; a water supply; a chemical and water mixer for receiving chemicals from the in situ chemical mixer and the water supply; a chemical and water distributor for distributing chemicals and water from the chemical and water mixer; a plurality of hoof baths for selectively receiving a mixture of chemicals and water from the chemical and water distributor; a bath flusher for receiving water from the water supply, the bath flusher for forcing water through the bath; and a system controller for synchronizing the chemical and water distributor and the bath flusher to flush the plurality of baths and refill the baths with a chemical and water mix.

The present invention also is directed to compositions and methods for combining or mixing compositions having two or more specific and complimentary antimicrobial components in a hoof bath just prior to use. Certain germicides when combined, act synergistically in such a way as to increase the efficacy of one or both of the germicides, as is the case with hydrogen peroxide and such germicidal inorganic salts as copper. In order for to gain maximum antimicrobial efficacy, the combined germicides must be used as soon as possible after combining before one or both of the germicides are used up due to oxidation or other type reactions with the other component. These components include one or more of certain antimicrobial salts of certain heavy metals including copper sulfate, copper acetate, copper formate, copper bromate, copper trichloroacetate, zinc sulfate, zinc acetate, zinc formate, zinc bromate or iron sulfate, iron acetate, iron formate, iron bromate or other heavy metal salts not listed. These components can also include such aldehydes as formaldehyde, gluteraldehyde or glycoxyaldehyde.

A second group of antimicrobial components should be mixed with the first to achieve the objectives of this invention. This second group can include quaternary ammonium compounds, such as monoalkyltrimethyl or triethylammonium salts such as monoalkyltrimethylammonium chloride, monoalkyldimethyl or monoalkyldimethyl-substituted benzylammonium salts, heteroaromatic ammonium salts, dialkyldimethylammonium salts, bis-quaternary ammonium salts, polysubstituted quaternary ammoniums salts and polymeric quaternary ammonium salts.

The second group can also include such inorganic peroxides such as hydrogen peroxide or persulfates, perborates, per carbonates and sodium peroxide, and organic peroxides such as peroxyacetic acid, or others such as other peroxy acids, cumene peroxide, hydroperoxides, diacyl peroxides and peroxyesters.

Sulfonic acids or sulfates can also be combined into the hoof bath and may include: dodecylbenzene sulfonic acid, sodium sulfanated oleic acid, sodium 1-octane sulfonate, sulfonated 9-ocatedceonic acid, sodium xylene sulfonate, dodecyldiphenyloxide disulfonic acid, sulfonated tall oil fatty acid, sodium naphtallene-sulfonic acid and 1-octane sulfonic acid.

Medium chain carboxylic fatty acids may also be added to the hoof bath and these may include: caproic, or hexanoic acid, heptanoic acid, caprylic or octanoic acid, nonanoic acid, capric or decanoic acid, lauric acid, myristic acid linoleic acid or linolenic acid or their esters such as methyl caprylate, methyl caprate, methyl laurate, lauryl acetate, glycerol monolaurate and amides of fatty acids, such as lauryl methylamide and dodecylamine.

The composition also might include raw elemental iodine and complexed iodinated compounds or iodophors. Carriers might include such surfactants as nonyl phenol ethoxylates, linear alcohol ehtoxylates, block co-polymers, or such polymers as polyvinylpyrridone (PVP).

The composition may also include chlorinated compounds such as chlorine dioxide or stabilized chlorine dioxide, salts of chlorine (sodium chorite) or organic chlorinated compounds (chloroisocyanurate), Phenolic compounds such as phenol and pheonlic esters of p-hydrobenzoic acid (methylparaben, propylparaben) may also be included in the second group of the composition.

All of the components in each group could be used in any combination and number of ingredients as long as there are at least two (at least one from each group) are being used at any one time. Each of these components can be used in any quantity or concentration as long as the concentration does not interfere or prevent another of these components from being added so that at least two compounds are able to be mixed at the site of use.

In addition to these components, there could be pre-added or added at the site at any concentration such components as acids including either organic acids such as acid, citric acid, acetic acid, inorganic acids such as phosphoric acid, sulfuric acid, nitric acid, surfactants, stabilizers, chelating agents, emulsifiers, thickeners, dyes and fragrances.

One advantage of combining two or more of the aforementioned antimicrobial hoof bath ingredients may be an increase in the ability to kill or inhibit disease-causing microorganisms. The killing action may be synergistic or merely additive, but in any case, will be better than using more of just component alone. These advantages, as conceived on a dairy operation, may be an increased killing rate, greater resistance to the effects of organic load, less toxicity from the chemicals and lower costs. If the action is synergistic, the most important advantage is that the combined mixture will chemically have an increased bactericidal efficacy against the disease pathogen than the sum of the parts would alone. If additive, the previously mentioned advantages by combining, for example, a more toxic but lower cost chemical with a less toxic one that costs more. In this case, toxicity will be avoided by combining the two instead of using more of the toxic chemical alone and some costs savings will be achieved by using the mixture instead of using just more of costlier component.

Some manufacturers have combined various types of antifoot disease chemicals or biologics and sold them as a ready-to-use pre-mixed product. This approach entails certain advantages such as a lack of stability that occurs when certain chemicals or biologics are combined. The previously mentioned combination of an inorganic salt combined with peroxide is a good example. The peroxide component will then oxidize quickly and after a relatively short period of time be rendered ineffective. Additional problems of storage or transport may occur if the combined constituents produce a mixture that may be volatile causing the release of gas at higher temperatures, which may therefore increase the risk of leaking or explosion if the containers are not properly vented.

BRIEF DESCRIPTION OF THE DRAWINGS

FIG. 15 is an elevational view of chemical powder mixing canisters in accordance with the present invention;

FIG. 16 is a suitable programming sequence for use in a hoof bath system in accordance with the present invention; and FIG. 17 is a PLC cycle chart for use in a hoof bath system in accordance with the present invention.

DETAILED DESCRIPTION OF THE PREFERRED EMBODIMENTS

Figure 1:
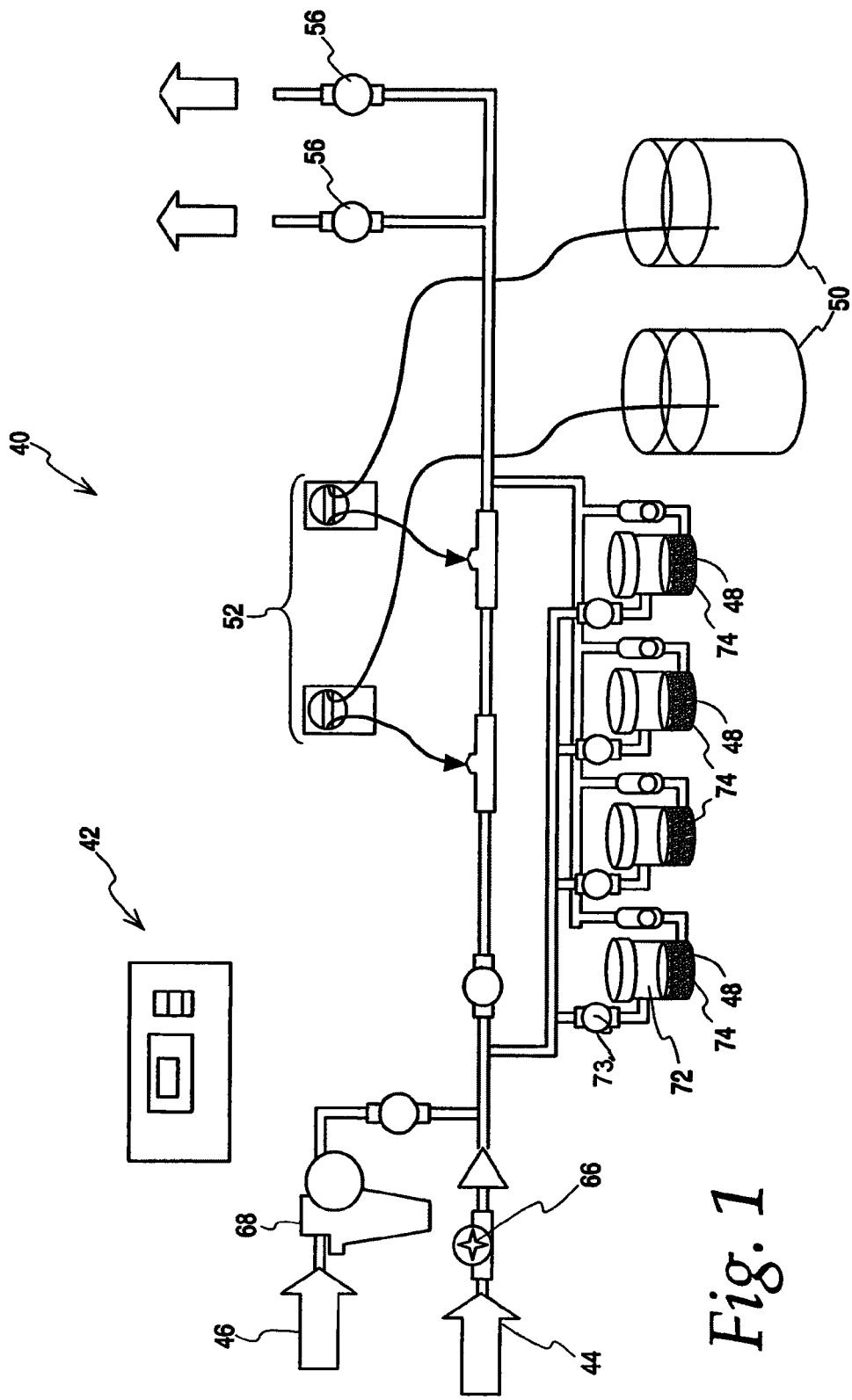
FIG. 1 is a schematic view of a hoof bath system in accordance with the present invention.

In the following detailed description of the preferred embodiments, the same reference numeral will be used to identify the same or similar feature in each of the figures.

Figure 2:
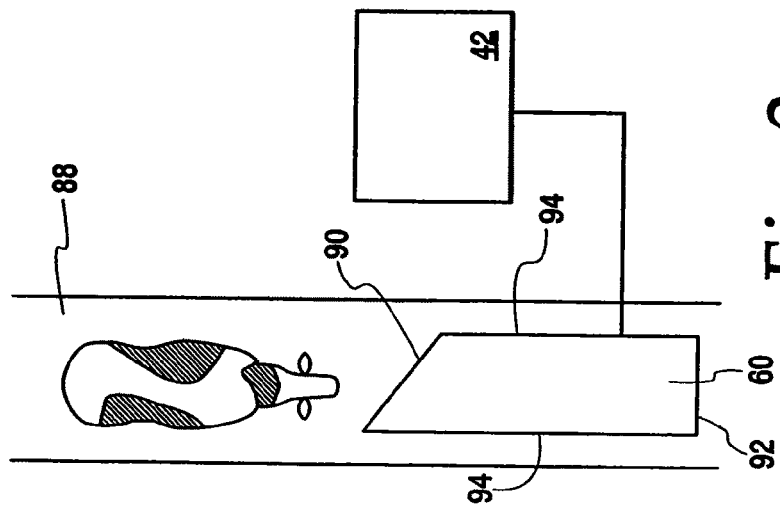
FIG. 2 is a schematic plan view of a hoof bath system in accordance with the present invention.

FIG. 1 is a schematic view of a hoof bath system 40 in accordance with the present invention, including a controller 42, a water supply 44, an air supply 46, a powder chemical dispenser 48, a liquid chemical dispenser 50, a pumping station 52, a water and chemical distribution network 54, and a control valve system 56. These components feed at least one hoof bath 60 as illustrated in FIG. 2. Also used in the system 40 is a drain 62.

The hoof bath system 40 provides a useful automated or semi-automated system for controlling hoof diseases in dairy animals by directing animals through at least one hoof bath 60 in which water and/or hoof treatment chemicals are disposed. The animal's hooves are thereby cleaned of a substantial amount of soil, such as dirt and manure. The chemicals can provide prevention or treatment of diseases that affect hooves.

The controller 42 can be any kind of programmable or manual controller of valves, pumps, drains and dispensers. Preferably, the controller 42 is programmable and fully automated to relieve a dairy operator from devoting valuable time and energy to hoof bath operation. The controller 42 can be any type of computer or printed circuit board. It can have the ability to receive various controlling operations and to receive data regarding hoof health for the dairy animals so that chemical type and quantity are automatically dispensed to address specific herd health needs.

In addition, flushing and re-filling frequency can be manually or automatically adjusted based on these factors. Finally, even when automation is not desired or feasible, the controller 42 can notify a dairy operator of conditions, flushing or re-filling operations, etc. so that the system 40 need not be monitored consistently.

The water supply 44 can be any standard water supply system for a dairy and need not supply potable water. Similarly, the air supply 46 is standard, but could be used to provide special gases necessary for mixing with chemicals. Suitable water filters 66 and air filters 68 are desirable.

In the present invention, both powder and liquid forms of chemicals can be used. It is desirable to use powder chemicals for reduced expense and increased shelf-life, but conditions and chemical types may control which type or combinations of chemicals are appropriate under given circumstances.

In the illustrated embodiment, powder chemical dispensers 48 are arranged in a pipe and valve network 70. Four canisters 72 are illustrated in FIG. 1 (and two are illustrated in FIG. 15), but one or more canisters could be used. Preferably, each individual canister 72 is partially filled with powdered chemicals 74 and then filled with a liquid mixing agent such as water or other liquid chemical. Each canister 72 is then filled with enough mixed chemical to supply an individual hoof bath. In this example, the appropriate amount of chemical is provided without complexing, mixing or metering from a bulk container.

Each canister—preferably is sized to receive enough powdered chemical to treat 150 to 200 cows depending upon soil load, chemical strength, and other factors. There can be multiple canisters to receive extra powdered chemical volume or a variety of chemicals. One canister is used each time a bath 60 is filled.

Once each canister is filled with powdered chemical it is filled with an appropriate amount of water to form a liquid solution. This solution can be concentrated to mix with more water prior to being added to the bath or in the bath itself, or the solution can be diluted to the proper amount in the canister.

The canisters are provided with fill valves 73 for the water or other liquid that will be mixed with the powdered chemical. The liquid may itself be a liquid chemical solution so that the combination of liquid chemical and powdered chemical provides an efficacious mixture of chemicals that need not have a long shelf-life prior to use in the bath. In this manner, varying chemical doses, mixtures and types is easily performed to obtain a highly effective hoof bath treatment chemical in an efficient and automated system 40.

Each canister also preferably includes a proximity sensor (not illustrated) that identifies the presence of powdered chemical or whether the canister is even closed properly. If neither of these conditions is met the canister will not fill with liquid, which could cause a spill.

Instead of, or in addition to the canister, the system may include mechanisms for injecting ozone ($O_3$) into the bath to disinfect the bath 60 and various pipes, nozzles, etc. in the chemical and/or water distribution system. No sanitizing chemicals may be necessary if this approach were used.

Figure 18:
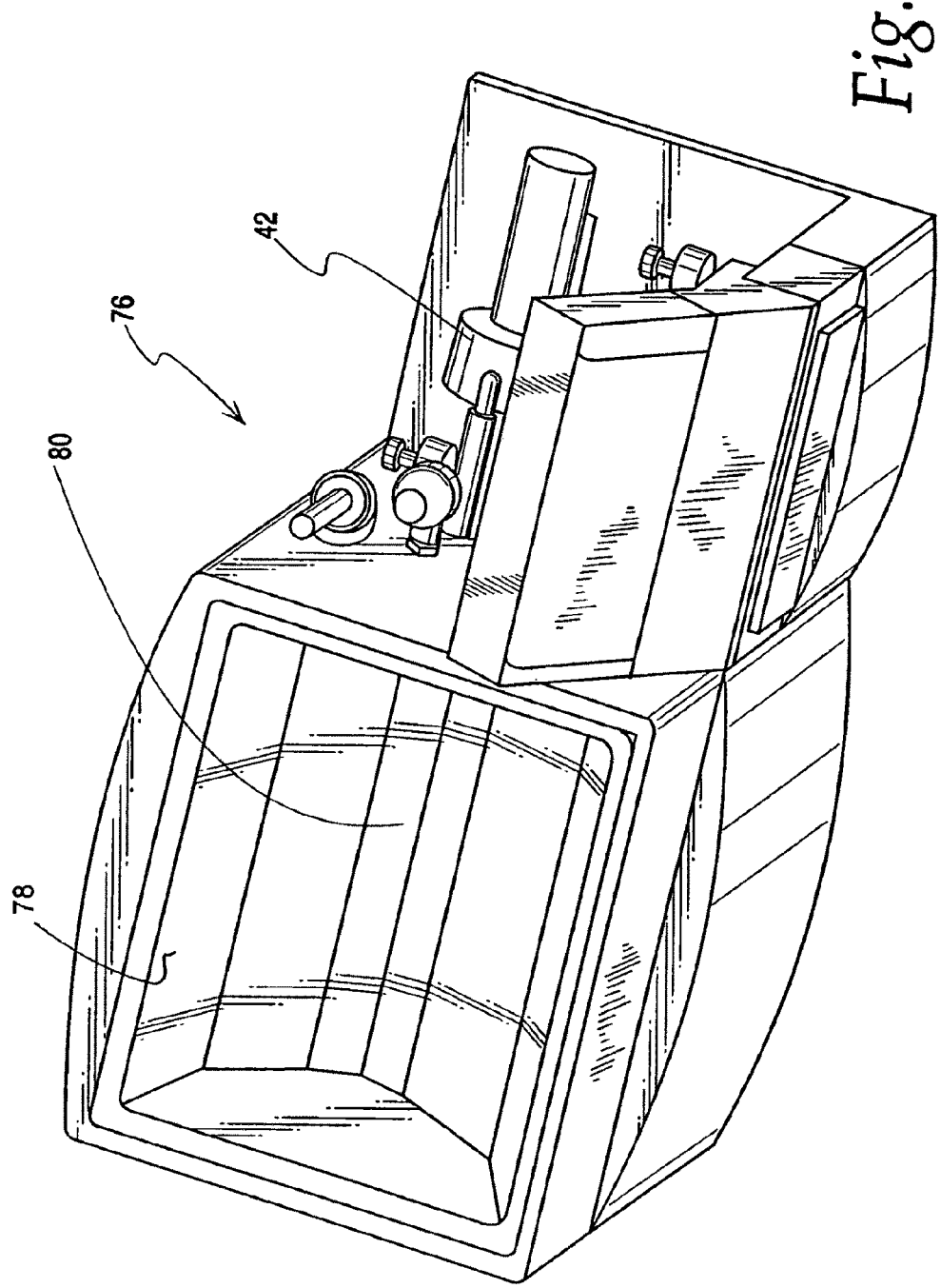
FIG. 18 is a perspective view of a bulk feed system in accordance with the present invention.

The individual canisters 72 can be filled by an operator or automatically by a bulk feed system 76. (FIG. 18.) The bulk feed system 76 includes a hopper 78 for receiving large loads of powdered chemical. An auger 80 in the hopper bottom moves chemical to a distribution shoot and then to individual canisters 72. When large containers (not illustrated) are used to mix powdered chemicals prior to use in the hoof baths, the bulk feed system 76 can be used to provide any desired amount of powder to the mixing container. Alternately, an adductor could be used to siphon chemical powder from a storage bin or hopper 78, which uses a venturi induced vacuum to carry chemical powder to a mixing canister or directly to a pipe in which the chemicals are mixed into solution.

The liquid chemical dispensers 50 can be used to store powdered chemicals after they have been mixed with water or to store liquid chemicals purchased in that form. They can be pumped into the water and chemical distribution system 54 as needed or in total, depending upon their capacity.

The chemicals in liquid form are pumped to the hoof baths 60 via the pumping station 60 through the water and chemical distribution network 54. The controller 42 can be used in conjunction with the pumping station 52 to pump only water from the water supply 44, only chemicals, or a mixture of the two, based on the operation stage of the hoof bath 60.

In addition, the controller 42 (FIG. 1) can be used to alternately operate the control valve system 56 to feed water, chemicals, and mixtures thereof to select hoof baths 60 when more than one are present.

In the present hoof bath system 40, any type or size of hoof bath can be used, and in particular a number of any such hoof baths can benefit from the system of the present invention. Nonetheless, a preferred hoof bath 60 is illustrated in FIGS. 2 through 6 and FIGS. 9 through 13.

As depicted, each hoof bath 60 is disposed in a walkway that controls animal movement and requires each animal to walk through the bath 60. Despite being forced to walk through the bath 60, its configuration in accordance with the present invention is preferably raised above the walkway for ease of installation and maintenance. Ramps or platforms (not illustrated) are provided for the animals.

Each bath 60 is generally longer than it is wide and has an upstream end 90, a downstream end 92, and sides 94. The upstream end 90 is disposed at an angle, approximately 45° in the illustrated embodiments, to the walkway so that the animals can step into the bath 60 without breaking stride. This arrangement is important to dairy efficiency because it keeps animals moving with minimal congestion and it keeps the animals comfortable.

Each lane is preferably sloped downward so that water and other liquids and soils flow in the same direction as cow traffic. The angled upstream end 90 of the bath therefore redirects the flow to the side so that it does not flow into the bath 60. In addition, a lip extending upstream away from the upstream end 90 of the bath 60 prevents higher velocity lane drainage from flowing into the bath.

In addition, the bath 60 is preferably dimensioned so that each animal hoof takes at least two steps in the bath 60 such that a preferred bath length is 108". Such a dimension improves overall bath performance by ensuring adequate rinsing and chemical treatment of each animal hoof. The bath 60 may also include gradations in the side walls to indicate the volume or depth of fluid in the bath 60 for operator inspection.

With typical soil loads, a hoof bath 60 in accordance with the present invention will require flushing every 150 to 200 animals being treated. A dairy operator can monitor this number and flush the hoof bath 60 or the flush can be automated.

When automated, the flushing operation can be initiated in several ways. One option is to automatically count cows as they pass through the bath 60 with either a proximity sensor or a wand switch (not illustrated) mounted in the lane. Counting cows automatically is a reliable way to ensure cleanliness of the bath 60 and efficacy of bath chemicals.

Another option is to initiate flushing in conjunction with the milking operation because the hoof bath 60 will typically be placed near a milking parlor exit. The bath 60 can be flushed and refilled at the start of milking by using one or more cow sensors in the milking parlor, for example. Another option is to initiate flushing at a predetermined time after the end of milking as sensed by the milker units. Refilling the bath 60 can then take place when the sensor senses the milker unit back in operation. In that way, the bath 60 will be filled shortly before the cow arrives.

Another option flushes and refills each bath 60 when the sensor signals an end to the milking cycle, provides a lag time for the last cow to move out of the parlor and through the bath 60, and then flushes and refills the bath in time for the next milking operation. Obviously, the number of cows, the frequency of milking, the shelf-life of treatment chemicals, bath soil loads, and other environmental conditions will be factors in determining when and how often the bath 60 needs to be flushed and refilled. The automated controller 42 is preferably programmable by the dairy operator to accommodate each particular dairy's varying needs.

Figure 3:
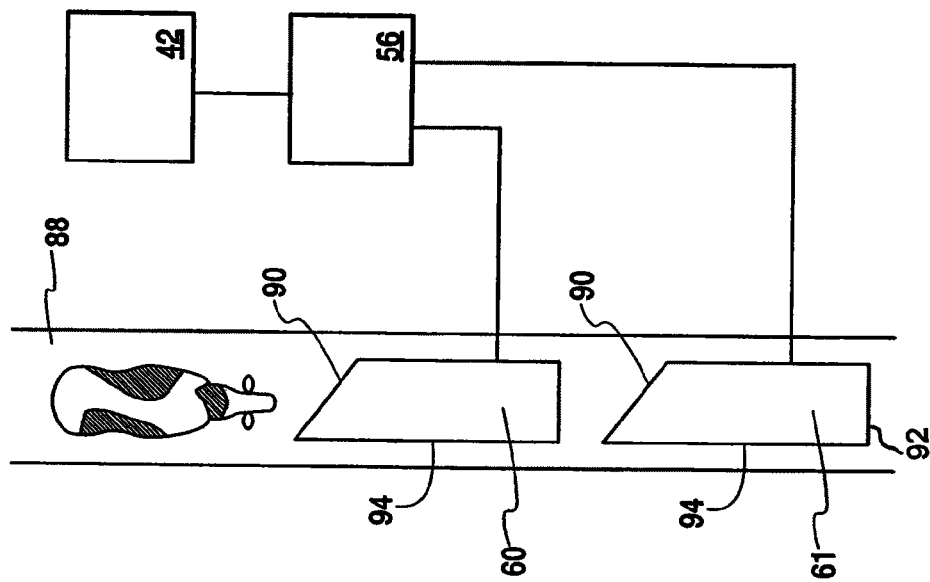
FIG. 3 is a schematic plan view of a hoof bath system in accordance with the present invention having a pair of baths in a series arrangement.

In FIG. 3, there is an upstream bath 60 and downstream bath 61 in series, which requires each animal to walk through both baths 60. In this arrangement, an upstream bath 60 can be used to rinse and clean the animal hooves, while the downstream bath 61 is used to treat the hooves. In such an arrangement, the upstream bath 60 may be water alone or include chemicals useful in cleaning hooves. In the downstream bath 61, medicines or other chemical treatments can be used.

The two baths 60, 61 are preferably fed from the same water and chemical distribution network 54 with the control valve system 56 and controller 42 working in conjunction to feed appropriate flushing, water, and treatment chemicals to each bath.

Figure 4:
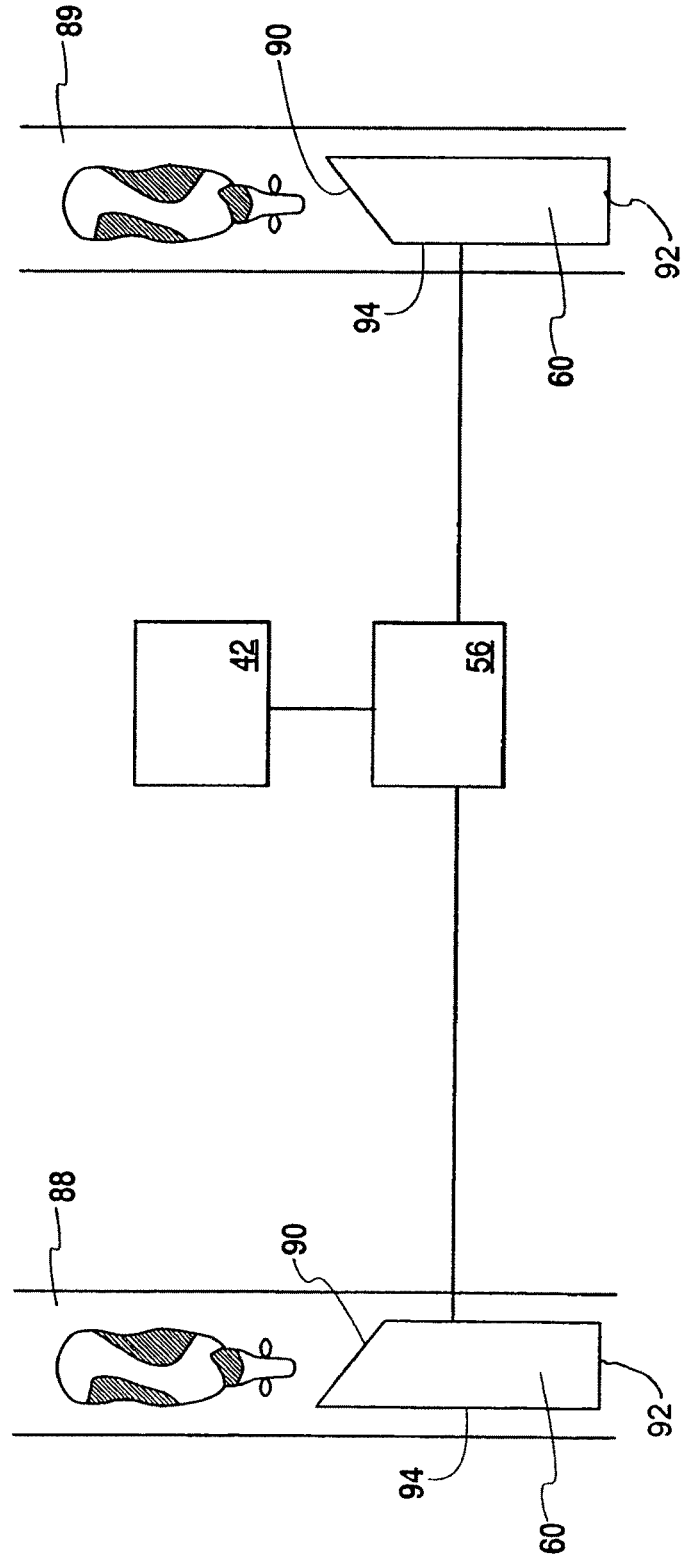
FIG. 4 is a schematic plan view of a hoof bath system in accordance with the present invention having a pair of baths in a parallel arrangement.

Similarly, the hoof bath system 40 may include a pair of baths 60 in a parallel arrangement, as illustrated in FIG. 4. With such an arrangement, two lanes of animal traffic can be accommodated as described above in reference to FIG. 2. In this arrangement, the controller 42 and control valve system 56 feed each bath 60 and 61. Each bath can receive the same water and chemical combinations, or each bath may receive different chemical and water solutions to treat animals in each lane differently. For example, animals with hoof diseases can be controlled through one lane for intensive treatment while other healthier animals are controlled through the other lane.

Figure 5:
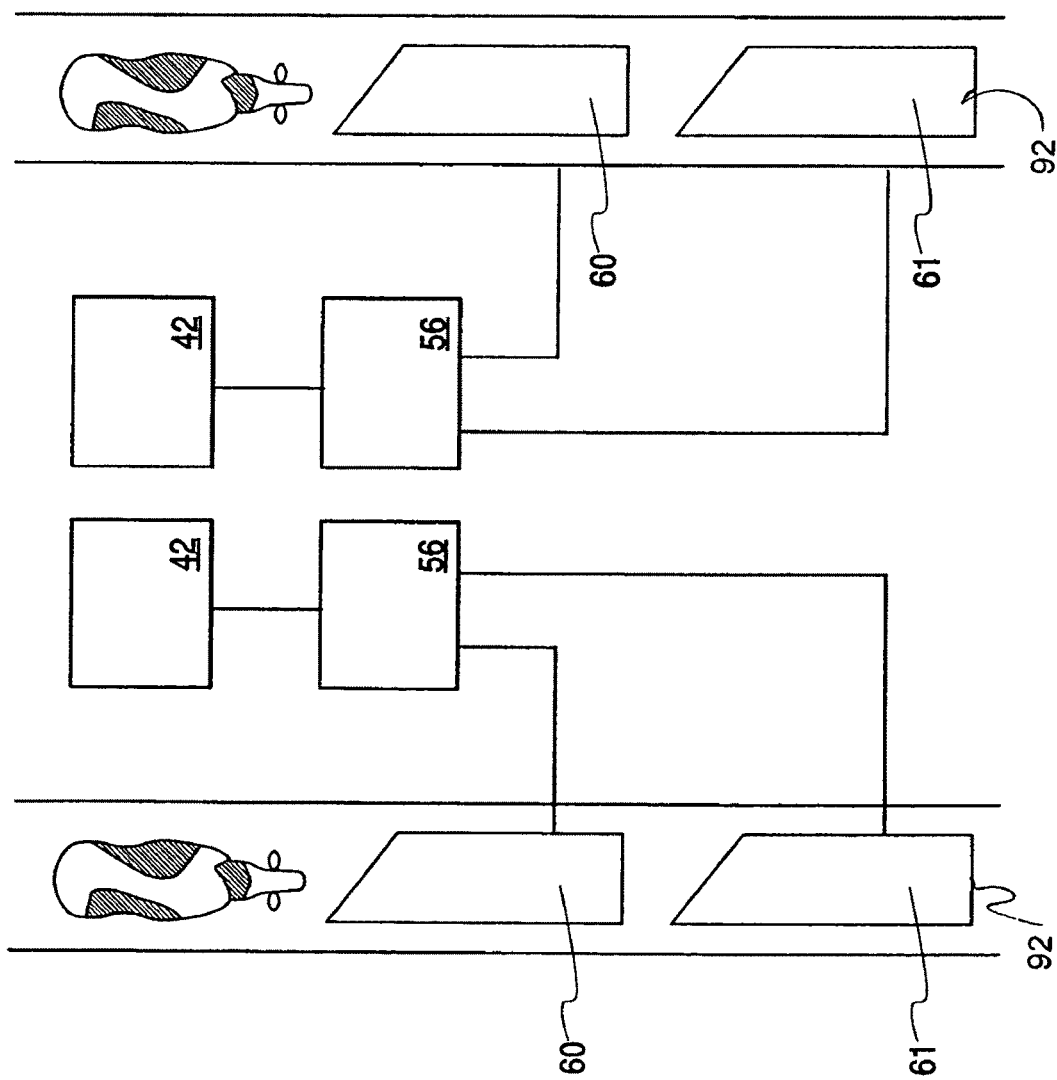
FIG. 5 is a schematic plan view of a hoof bath system having two lanes of baths in series.

A combination of series baths from FIG. 3 and parallel baths from FIG. 4 are illustrated if FIG. 5 so that any desired form of pre-treatment and treatment can be used.

Figure 6:
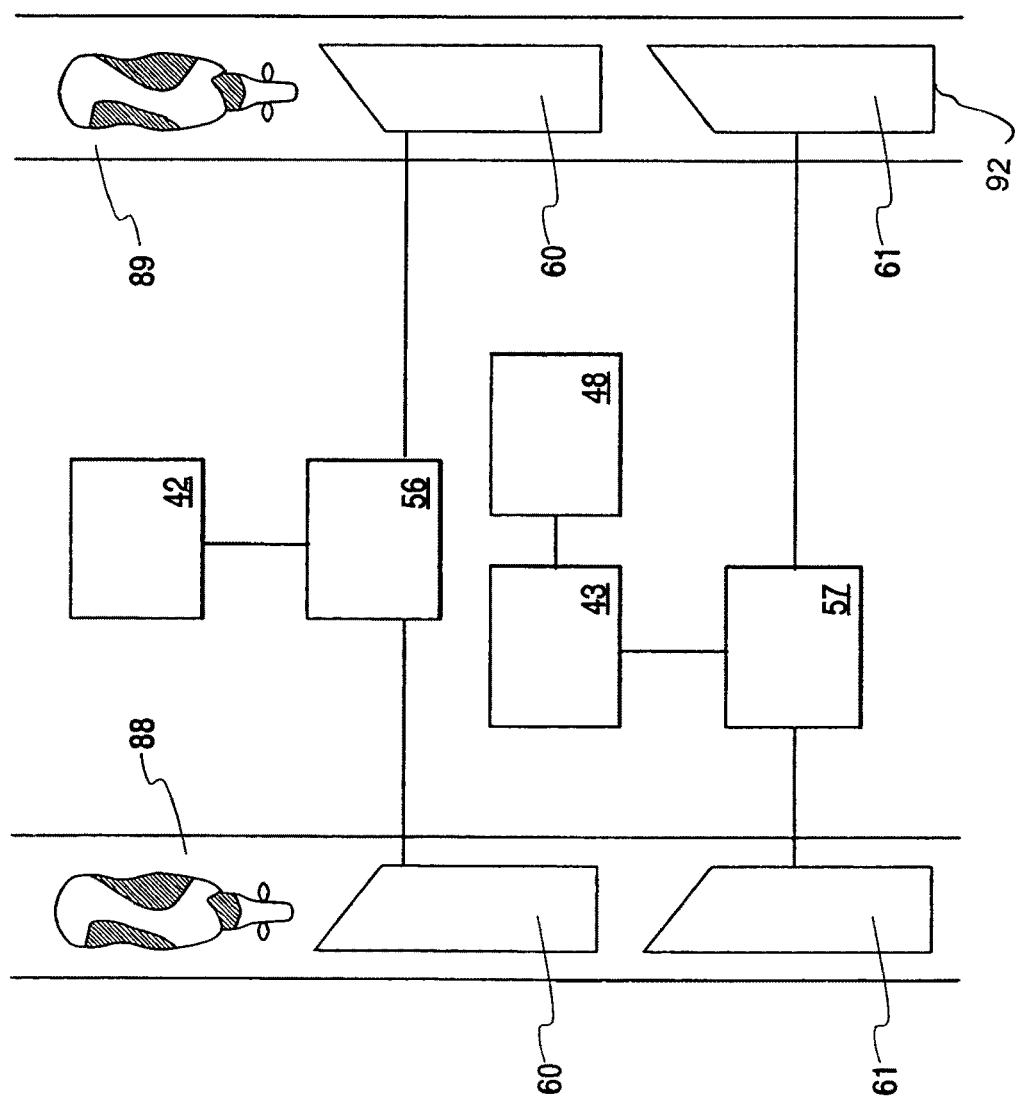
FIG. 6 is a schematic plan view of a hoof bath system having two lanes of baths in series and having a chemical powder mixer/dispenser.

In FIG. 6, there is a system 40 similar to the system 40 in FIG. 5 except that the upstream baths 60 are fed by a first controller 42 and control valve system 56 and the downstream baths 61 are fed from a separate controller 43 and control valve system 57. The second controller 43 may be used in situations when chemicals are only fed to the downstream baths 61 and not the upstream baths 60.

Figure 7:
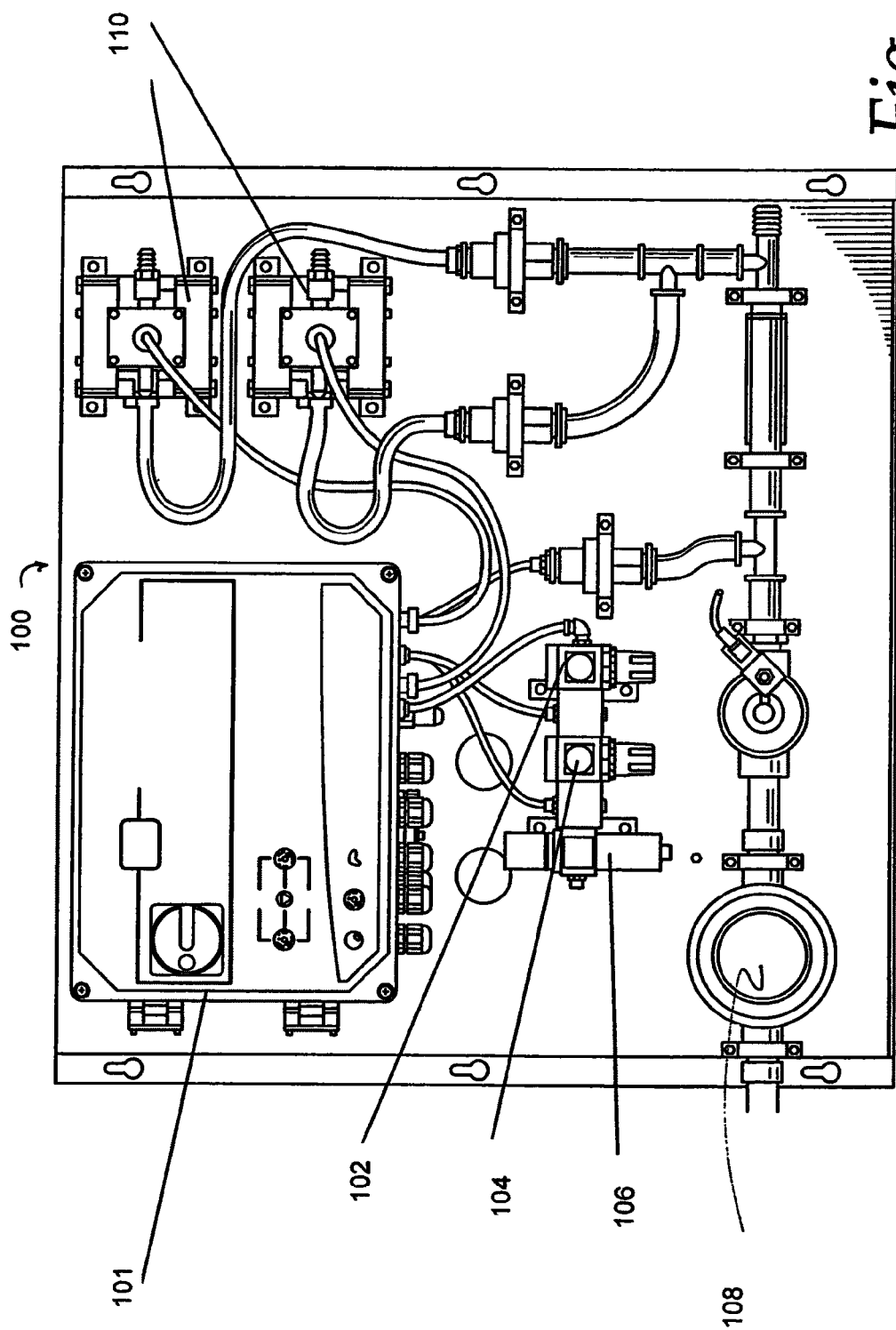
FIG. 7 is an elevational view of a control panel for use in a hoof bath system in accordance with the present invention.

FIGS. 7 and 15 illustrate a control panel 100 that is at least part of the controller 42. The controller 42 may include computers and other control panels as well. The control panel 100 illustrated includes a PLC control, switching for purge air regulators 102, bladder air regulator 104, pump air regulator 106, a water meter 108, and liquid chemical pumps 110. With such an arrangement in the control panel 100, an operator can monitor and operate the hoof bath system 40 of the present invention at any location.

Figure 8:
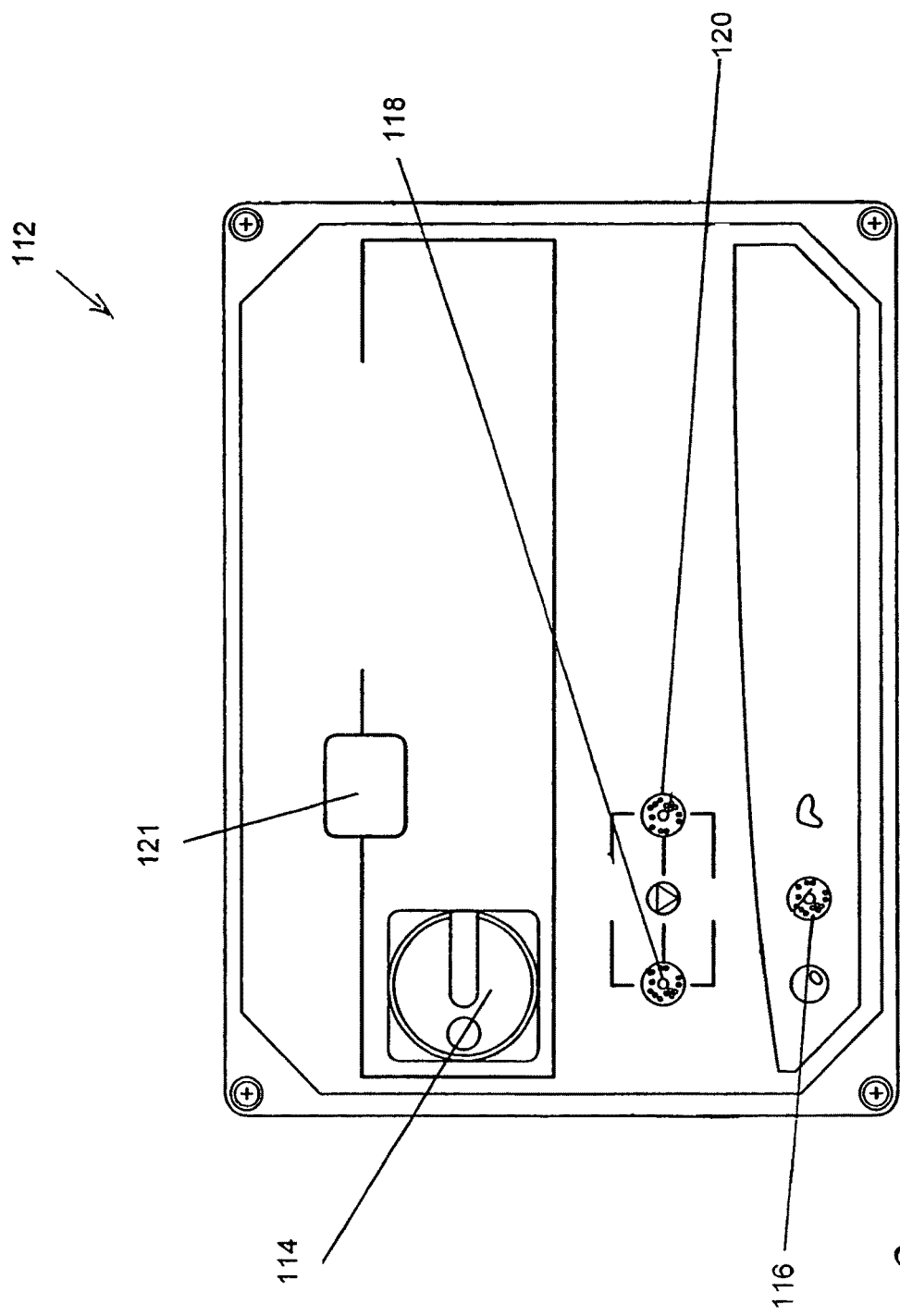
FIG. 8 is a cover panel for the control panel of FIG. 7.

FIG. 8 simply illustrates the cover 112 for the control panel including a main power on/off switch 114, chemical and water control switches 116, automatic stop/flush switch 118 for a first bath, a similar switch 120 for a second bath, and a display 121.

Figure 9:
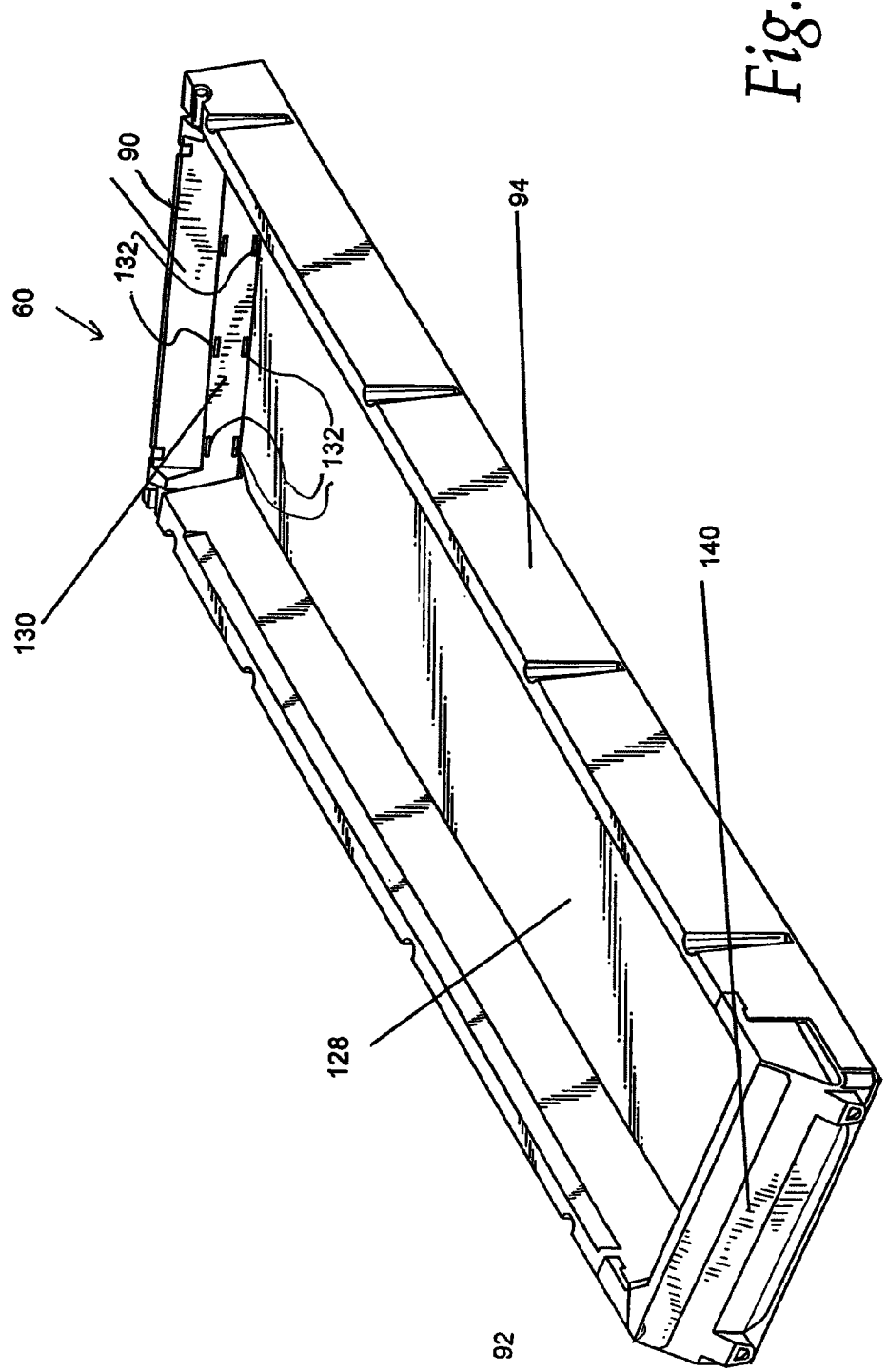
FIG. 9 is a perspective view of a hoof bath in accordance with the present invention.

More detailed illustrations of the hoof bath 60 appear in FIGS. 9 through 13. In FIG. 9 the bath 60 includes the upstream end 90, downstream end 92, and sides 94 as generally described above.

The bath 60 is preferably made of heavy-duty cross-linked polyethylene plastic, but other materials can be used as well. In addition, a rubber mat 128 is disposed in the bottom for better footing. The mat 128 can be replaced with other similar mats or mats of differing properties as weather and bath soil conditions vary.

The upstream end 90 includes a liquid distribution manifold 130 that injects water and chemicals into the bath 60. Disposing the manifold 130 in this location is desirable because animals are less likely to kick and damage the manifold 130.

The manifold 130 includes orifices 132 through which liquid flows. (FIG. 9). At alternating times, there may be water only, chemical only, or mixtures thereof flowing out of the manifold orifices 132. The orifices are arranged downstream toward the downstream end 92 of the bath 60 despite the fact that they are disposed in the angled upstream end 90 of the bath 60. Side baffles 133 extending inwardly from the sidewalls 94 can be used to reduce some splashing from the manifold 130 injections.

Figure 11:
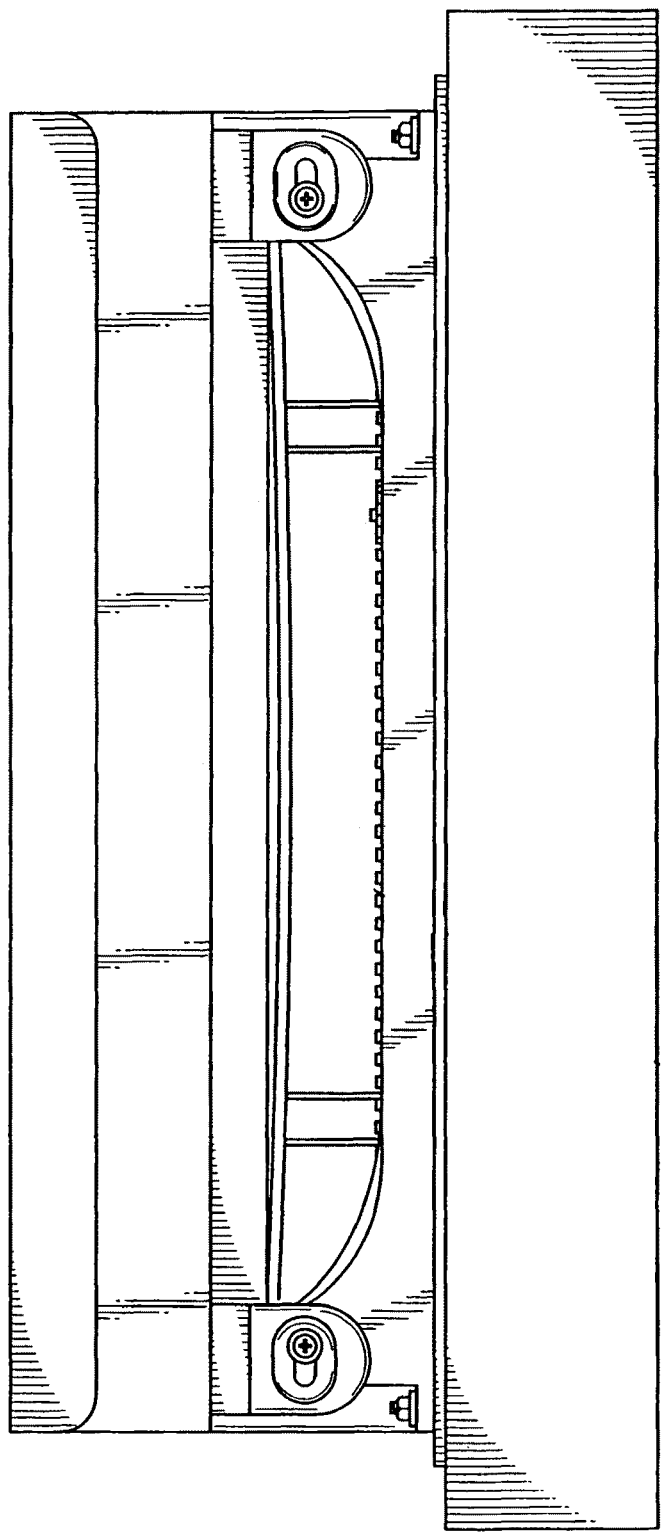
FIG. 11 is an elevational view of a pneumatic bladder in a deflated position to drain fluid from a hoof bath in accordance with the present invention.

In the preferred embodiment, the downstream end 92 of the bath 60 includes a pneumatic bladder "gate" 140 that is inflated to close off the downstream end 92 (FIG. 12) and thereby retain fluid in the bath 60. The bladder 140 is deflated to release fluid and debris from the bath 60 (FIG. 11). The pneumatic bladder 140 provides a superior seal against leakage as compared to moving plates and is less likely to clog than a drain or valve arrangement.

By simply deflating the bladder 140 (FIG. 11), liquid in the bath 60 can drain or be flushed by water from the liquid distribution manifold 130. The bladder 140 is less likely to be damaged by animals. Further, when the bladder 140 is re-inflated after flushing (FIG. 12), it can conform to the shape of obstacles or debris that was not completely flushed from the bath 60. This is not necessarily possible with a moving plate, drain, or valve that could be used in place of the bladder 140.

Figure 10:
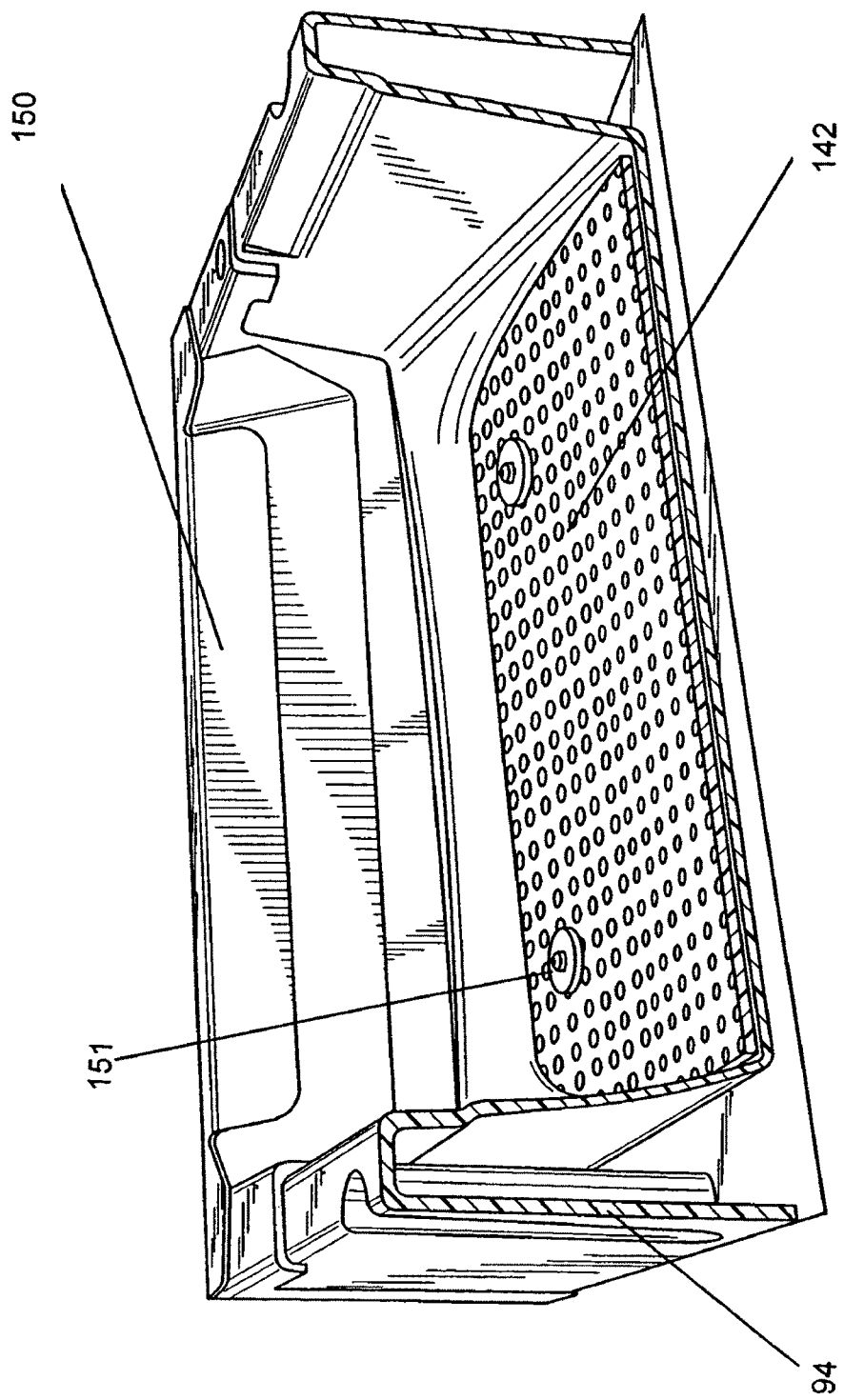
FIG. 10 is a cross-sectional perspective view of a hoof bath in accordance with the present invention.

FIG. 10 illustrates further details of the hoof bath 60, including a stainless steel protective cover 150 for protecting the manifold 130. If desired, the mat 142 can be secured to the bath 60 using stainless steel fittings 151.

Figure 12:
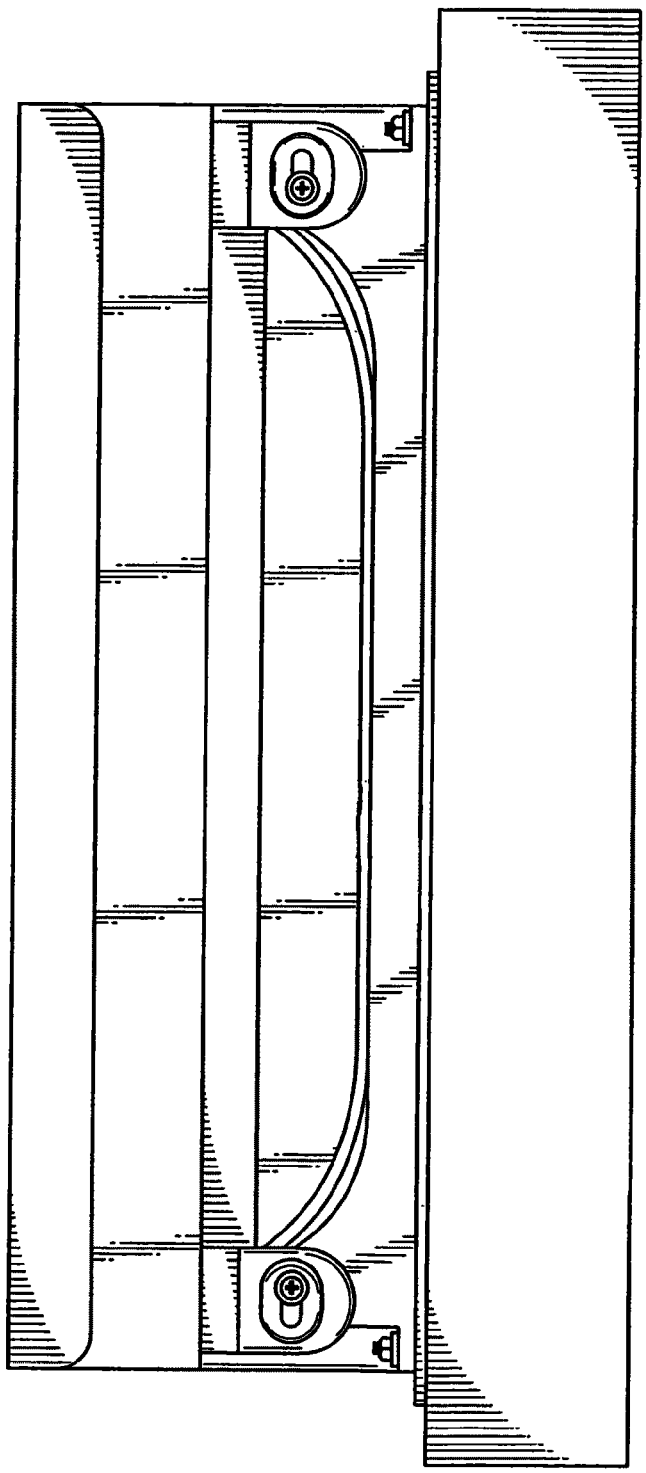
FIG. 12 is an elevational view of the pneumatic bladder of FIG. 11 in an inflated position to retain fluid in a hoof bath.
Figure 13:
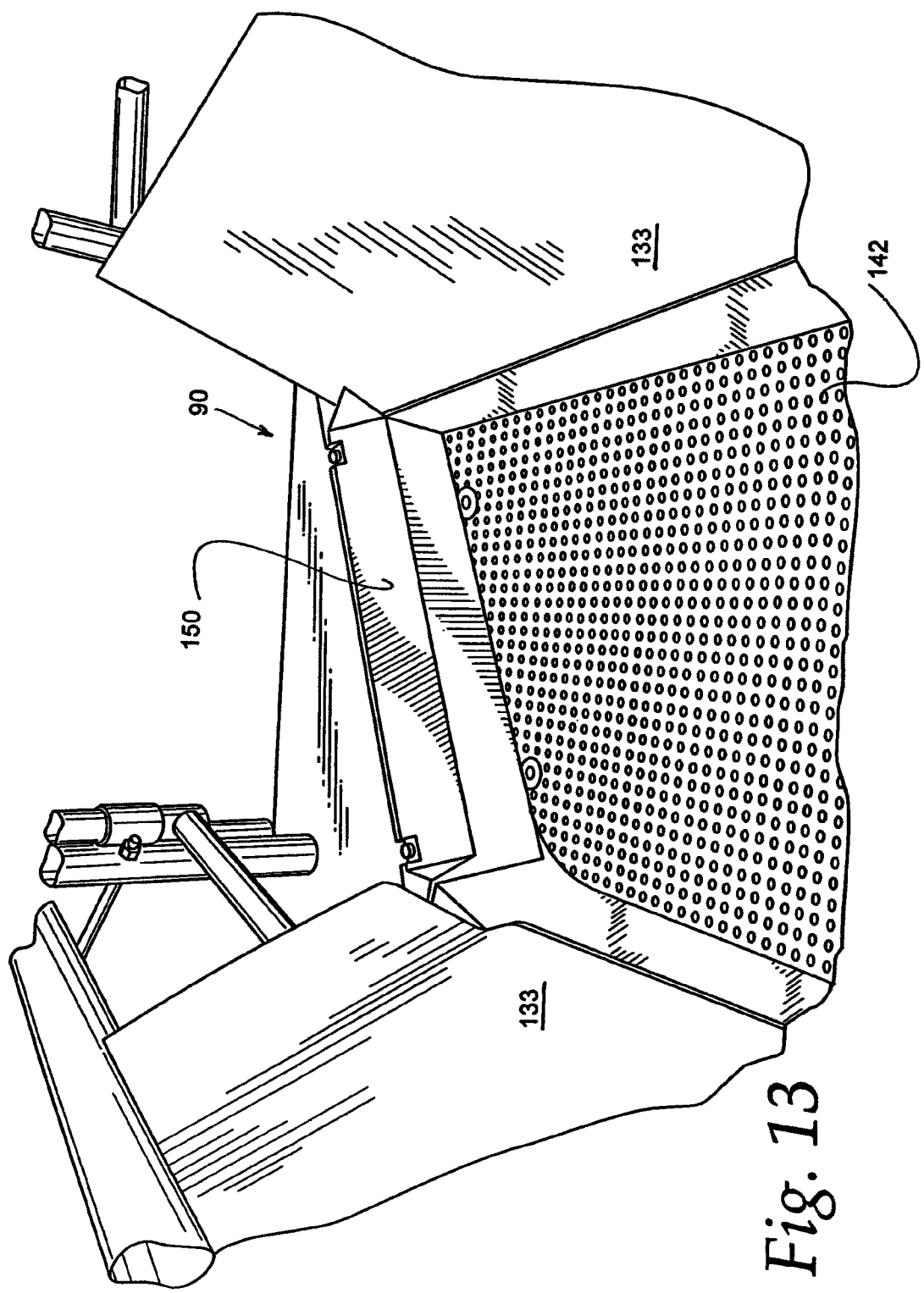
FIG. 13 is a perspective view of an angled hoof bath upstream end.
Figure 14:
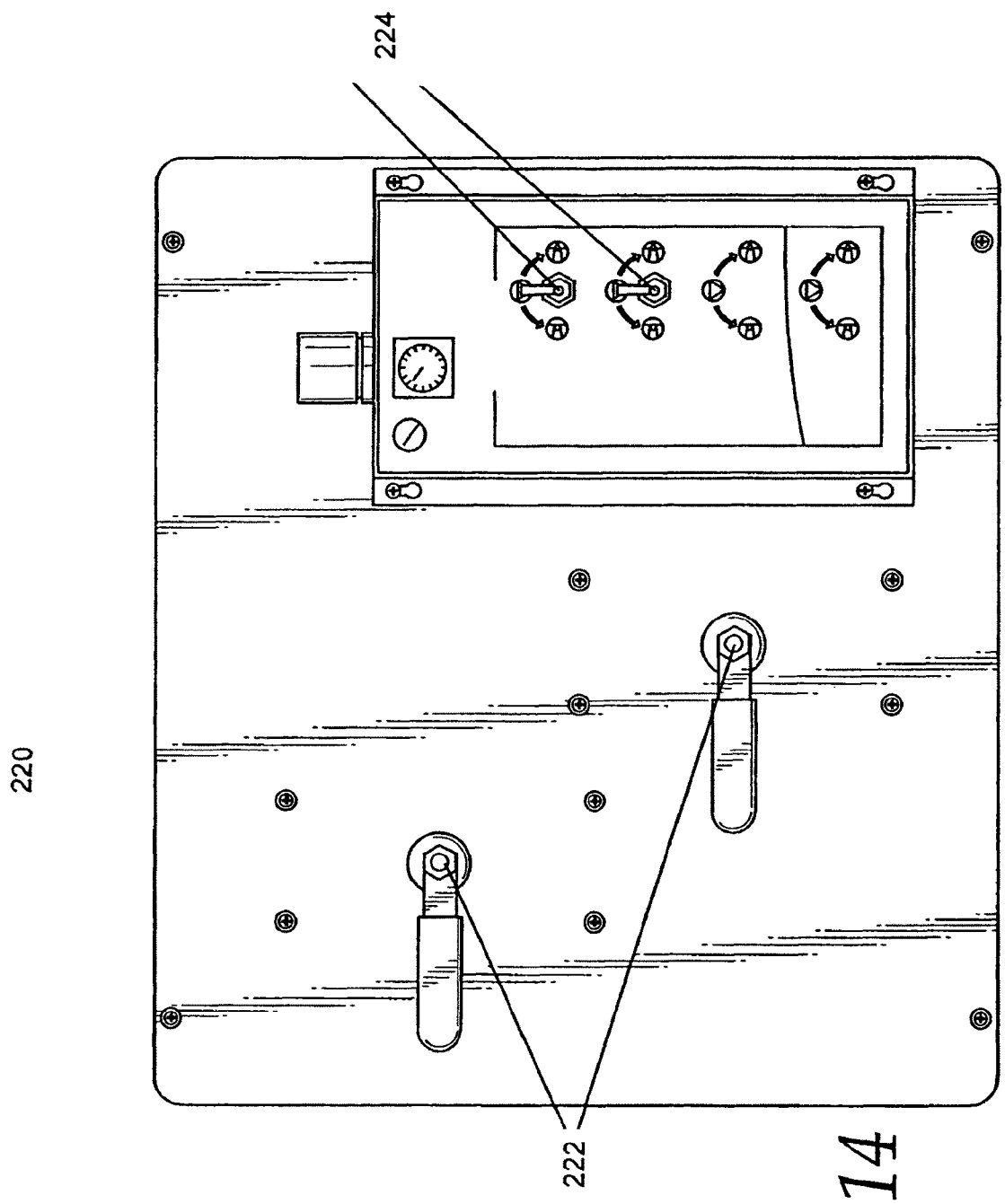
FIG. 14 is a control panel for a hoof bath system having an operator-controlled pneumatic bladder valve.

FIGS. 11 and 12 illustrate the bladder 140 in the opened and closed positions, respectively. The bladder 140 in the opened position opens up nearly the entire width of the bath downstream end 92 to improve drainage and complete flushing of soil and debris from the bath 60.

In the inflated position, a mere nine pounds per square inch (9 psi) is adequate to seal the downstream end 92 of the bath 60.

The bladder 140 can be operated with manual switches and pumps or it can be operated automatically by the controller 42.

FIG. 16 illustrates a suitable programming schedule 200 and FIG. 17 illustrates a suitable cycle chart 210 for use in a hoof bath system 40 in accordance with the present invention.

One purpose of the present system is directed to compositions and methods for mixing certain, specific and known antimicrobial components at the site of the hoof bath just prior to use by the cows. This invention enables a dairy farmer in the control of contagious diseases of the bovine foot while increasing cost savings and increasing safety to humans and animals. Evidence in the laboratory and in the field supports these contentions especially as it relates to bactericidal efficacy. It also lessens the problems associated with pre-mixing ingredients such as stability and safety in storage and transport.

The antimicrobial hoof bath chemicals and biologics are combined at the site of the hoof bath just prior to use. These components can be solid, liquid or both combined. They can be dispensed manually or by systems presently developed or in development that dispense the chemicals automatically into the hoof bath via pipes or hoses (for liquids) or automated hoppers (for solids). These devices can be set to dispense at pre-determined intervals based on time or number of cows and thereupon dispense a pre-set amount of chemicals along with water to achieve the desired dilution rate.

Prior to the addition of new chemical(s), the old, used solution along with contaminating manure or soil can be forced out or flushed automatically out of the hoof bath into a drain. The present invention of mixing components at site provides the greatest benefit when used with an automated system although it can also be practiced manually.

One example utilizing an automated flushing hoof bath entails adding, at specified intervals, pre-diluted copper sulfate, pre-diluted quaternary ammonium compound and pre-diluted hydrogen peroxide and water where the final concentration of each component would be 2% by volume. This would provide advantages over using only one of these compounds, even at a higher concentration or using them alternatively at different times or pre-mixing them at a considerable time prior to use (i.e.: time of manufacture).

The advantages would include cost savings by using less chemical and less labor to apply chemical to the hoof bath or utilize less storage space because lower amounts of the bulkier products can be used. Efficacy advantages would be expected with a greater reduction or lower rate of infection of the aforementioned foot/hoof diseases. Automated systems ensure that the chemicals or biologics are at the doses specified since the chance of degradation of components (such as the hydrogen peroxide) would be lessened if they are not mixed a significant time prior to use.

The present invention in its preferred embodiments described herein conserves water by using fewer than ten gallons of flushing liquid; has chemical resistant and durable high-strength plastic construction; utilizes a large drainage zone sealed by an effective bladder to seal the drainage zone; has a longer (108") length that assures double treatment (two steps) of rear hooves; is automated to reduce operation interaction if desired; is programmable as dairy conditions change; accurately mixes treatment chemicals; optionally mixes a variety of chemicals that have higher potency but possibly short shelf-life; and has an automated flush and refill option that can be activated by an operator, cow counts, or milking equipment activation/deactivation. The result is a cost-effective and efficacious hoof treatment system.

The foregoing detailed description of the present invention is provided for clearness of understanding only. No unnecessary limitations therefore should be read into the following claims.

The invention claimed is:

1. A hoof bath system for dairy animals comprising:
   a hoof bath having an inlet, an upstream end, a pair of spaced-apart sides joined to the upstream end, and a downstream end joined to the pair of spaced-apart sides, and a drain at the downstream end, and
   the drain includes an upper support member and a lower surface to define a drain opening that is opened and closed solely by an inflatable bladder moving between a drain open position and a drain closed position, wherein the hoof bath inflatable bladder moves from the upper support member toward the lower surface when moving toward the drain closed position, and the bladder can conform to animal debris in the drain.

2. The hoof bath system of claim 1, and
   the foot bath further comprising:
   a side joined to the upstream end to define an angle therebetween that is less than 90°.

3. The hoof bath system of claim 1, and further comprising a chemical feed system that delivers treatment chemicals.

4. The hoof bath system of claim 3, wherein the chemical feed system delivers treatment chemicals that further comprise:
   quaternary ammonium compounds.

5. The hoof bath system of claim 3, wherein the chemical feed system delivers treatment chemicals that further comprise:
   monoalkyltrimethyl or triethylammonium salts such as monoalkyltrimethylammonium chloride, monoalkyldimethyl or monoalkyldimethyl-substituted benzylammonium salts, heteroaromatic ammonium salts, dialkyldimethylammonium salts, bis-quaternary ammonium salts, polysubstituted quaternary ammoniums salts and polymeric quaternary ammonium salts.

6. The hoof bath system of claim 3, wherein the chemical feed system delivers treatment chemicals that further comprise:
   inorganic peroxides.

7. The hoof bath system of claim 3, wherein the chemical feed system delivers treatment chemicals that further comprise:
   peroxides selected from the group consisting of: hydrogen peroxide or persulfates, perborates, per carbonates and sodium peroxide, peroxyacetic acid, peroxy acids, cumene peroxide, hydroperoxides, diacyl peroxides, peroxyesters, and combinations thereof.

8. The hoof bath system of claim 3, wherein the chemical feed system delivers treatment chemicals that further comprise:
   sulfonic acids.

9. The hoof bath system of claim 3, wherein the chemical feed system delivers treatment chemicals that further comprise:
   sulfates.

10. The hoof bath system of claim 3, wherein the chemical feed system delivers treatment chemicals that further comprise:
    ingredients selected from the group consisting of: dodecylbenzene sulfonic acid, sodium sulfanated oleic acid, sodium 1-octane sulfonate, sulfonated 9-ocatedceonic acid, sodium xylene sulfonate, dodecyldiphenyloxide disulfonic acid, sulfonated tall oil fatty acid, sodium naphtallene-sulfonic acid, 1-octane sulfonic acid, and combinations thereof.

11. The hoof bath system of claim 1, wherein the inlet comprises:
    an inlet manifold having a plurality of nozzles for emitting fluid into the foot bath.

12. The hoof bath system of claim 1, wherein the inflatable bladder comprises:
    a pneumatic bladder.

* * * * *